US010751001B2

(12) United States Patent
Warner et al.

(10) Patent No.: US 10,751,001 B2
(45) Date of Patent: Aug. 25, 2020

(54) SYSTEMS AND METHODS FOR TRACKING AND ANALYSIS OF ELECTRICAL-PHYSIOLOGICAL INTERFERENCE

(71) Applicant: General Electric Company, Schenectady, NY (US)

(72) Inventors: Adrian Warner, Wauwatosa, WI (US); Dan Schneidewend, Menomonee Falls, WI (US); Claudio Mejia, Wauwatosa, WI (US); Vivek Sachdev, Wauwatosa, WI (US)

(73) Assignee: General Electric Company, Schenectady, NY (US)

( * ) Notice: Subject to any disclaimer, the term of this patent is extended or adjusted under 35 U.S.C. 154(b) by 1243 days.

(21) Appl. No.: 14/095,632

(22) Filed: Dec. 3, 2013

(65) Prior Publication Data
US 2015/0150512 A1    Jun. 4, 2015

(51) Int. Cl.
*A61B 5/00*    (2006.01)
*A61B 5/04*    (2006.01)
*A61B 5/0402*    (2006.01)

(52) U.S. Cl.
CPC ............. *A61B 5/7203* (2013.01); *A61B 5/04* (2013.01); *A61B 5/0402* (2013.01); *A61B 2560/0242* (2013.01)

(58) Field of Classification Search
CPC ....... A61B 5/7203; A61B 5/04; A61B 5/0402; A61B 2560/0242
See application file for complete search history.

(56) References Cited

U.S. PATENT DOCUMENTS

| 4,123,620 A | 10/1978 | Karlsson |
| 4,420,815 A | 12/1983 | Francis |
| 6,188,771 B1 | 2/2001 | Horrall |
| 6,370,254 B1 | 4/2002 | Gore et al. |
| 6,984,207 B1 * | 1/2006 | Sullivan ............... A61B 5/0002 600/300 |

(Continued)

FOREIGN PATENT DOCUMENTS

| WO | WO 1999 04688 | 2/1999 |
| WO | WO 2000 005665 | 2/2000 |

*Primary Examiner* — Gary Jackson
*Assistant Examiner* — Jessandra F Hough
(74) *Attorney, Agent, or Firm* — The Small Patent Law Group LLC; Dean D. Small

(57) ABSTRACT

A method for noise information management is provided including obtaining, via at least one physiological sensor, physiological information of a patient, and obtaining, via a noise acquisition unit, noise information corresponding to noise occurring during collection of the physiological information. The method also includes recording the physiological information on at least one physiological recording channel and recording the noise information on at least one noise recording channel at a sample rate corresponding to a rate used to record the physiological information. Also, the method includes associating the noise information with environmental information corresponding to at least one of a time or location at which the physiological information was acquired from the patient to provide a case noise profile. Further, the method includes storing the case noise profile as part of an archive containing plural case noise profiles.

26 Claims, 4 Drawing Sheets

(56) References Cited

U.S. PATENT DOCUMENTS

| | | |
|---|---|---|
| 8,284,926 B2 | 10/2012 | Diethorn |
| 8,334,784 B2 | 12/2012 | Patel et al. |
| 8,515,530 B2 | 8/2013 | Warner et al. |
| 2001/0021259 A1 | 9/2001 | Horrall |
| 2003/0198339 A1 | 10/2003 | Roy et al. |
| 2004/0042615 A1 | 3/2004 | Scholte |
| 2004/0116130 A1 | 6/2004 | Seligmann |
| 2005/0213731 A1 | 9/2005 | Rodman et al. |
| 2006/0142070 A1 | 6/2006 | Park |
| 2006/0177046 A1 | 8/2006 | Falcon |
| 2007/0003072 A1* | 1/2007 | Ward ............... A61B 7/00 381/71.1 |
| 2007/0050451 A1 | 3/2007 | Caspi et al. |
| 2007/0053524 A1 | 3/2007 | Haulick et al. |
| 2007/0202858 A1 | 8/2007 | Yu |
| 2008/0045832 A1 | 2/2008 | McGrath |
| 2008/0089513 A1 | 4/2008 | Kotzin et al. |
| 2008/0315879 A1* | 12/2008 | Saha ............... A61B 5/055 324/318 |
| 2011/0276275 A1* | 11/2011 | Addison ......... A61B 5/14551 702/19 |
| 2015/0257680 A1* | 9/2015 | Inan ............... A61B 5/029 600/301 |

\* cited by examiner

SYSTEMS AND METHODS FOR TRACKING AND ANALYSIS OF ELECTRICAL-PHYSIOLOGICAL INTERFERENCE

BACKGROUND OF THE INVENTION

The subject matter disclosed herein relates generally to tracking and analysis of electrical-physiological interference, and more particularly to automated tracking and analysis of electrical-physiologic interference occurring during a medical procedure and/or occurring in a hospital or other managed care institution.

Electrical interference, or noises, may pose significant problems with the use of sensitive medical instruments and/or imaging devices. The U.S. Food and Drug Administration (FDA) has made recommendations to capture and log noise events to help determine the characteristics of the interferences. Conventional logging techniques may rely on operator judgment and diligence in recording interference, however, and are frequently unreliable and/or incomplete. Conventional logging techniques are labor intensive and error prone. There may be a number of sources of interference for any given application, ranging from incorrect application or use of a medical device, to environmental factors within or nearby a hospital infrastructure, to unintended influences from external power sources or consumers. Maintaining the necessary discipline to log events is difficult and time consuming. Further, logged data is often anecdotal, or forms part of a patient record making extraction difficult while maintaining necessary privacy concerns.

Use of external services, for example to identify sources or causes of interference, suffers from drawbacks as well. For example, conditions used to test a facility may not be an accurate replication of actual conditions, for example with respect to all of the equipment used. The equipment and patient may be understood as forming a complex web or array of receiver/transmitter elements, which may be difficult to duplicate. Staff misuse of equipment may make an acceptable situation appear worse than reality, and a false positive may result. Also false positives may drive up expense and/or result in temporary loss of utility of facilities.

BRIEF DESCRIPTION OF THE INVENTION

In accordance with various embodiments, a method for noise information management is provided. The method includes obtaining, via at least one physiological sensor, physiological information of a patient, and obtaining, via a noise acquisition unit, noise information corresponding to noise occurring during collection of the physiological information. The method also includes recording the physiological information on at least one physiological channel and recording the noise information on at least one noise channel at a sample rate corresponding to a rate used to record the physiological information. Also, the method includes associating the noise information with environmental information corresponding to at least one of a time or location at which the physiological information was acquired from the patient to provide a case noise profile. Further, the method includes storing the case noise profile as part of an archive containing plural case noise profiles.

In accordance with various embodiments, a method for noise information management is provided. The method includes obtaining, via at least one physiological sensor, physiological information of a patient, and obtaining, via a noise acquisition unit, noise information corresponding to noise occurring during collection of the physiological information. The method also includes recording the physiological information on at least one physiological channel and recording the noise information on at least one noise channel at a sample rate corresponding to a rate used to record the physiological information. Further, the method includes associating the noise information with environmental information corresponding to at least one of a time or location at which the physiological information was acquired from the patient to provide a case noise profile. Also, the method includes performing, with at least one processing unit, an analysis of the case noise profile using information at least one of contained in or developed from an archive containing plural case noise profiles.

In accordance with various embodiments, a system is provided including an input module, an association module, and an archive module. The input module is configured to obtain, via at least one physiological sensor, physiological information of a patient, and to obtain, via a noise acquisition unit, noise information corresponding to noise occurring during collection of the physiological information. The association module is configured to record the physiological information on at least one physiological channel, and to record the noise information on at least one noise channel at a sample rate corresponding to a rate used to record the physiological information. The association module is also configured to associate the noise information with environmental information corresponding to at least one of a time or location at which the physiological information was acquired from the patient to provide a case noise profile. The archive module is configured to store the case noise profile as part of an archive containing plural case noise profiles.

DETAILED DESCRIPTION OF THE INVENTION

Figure 1:
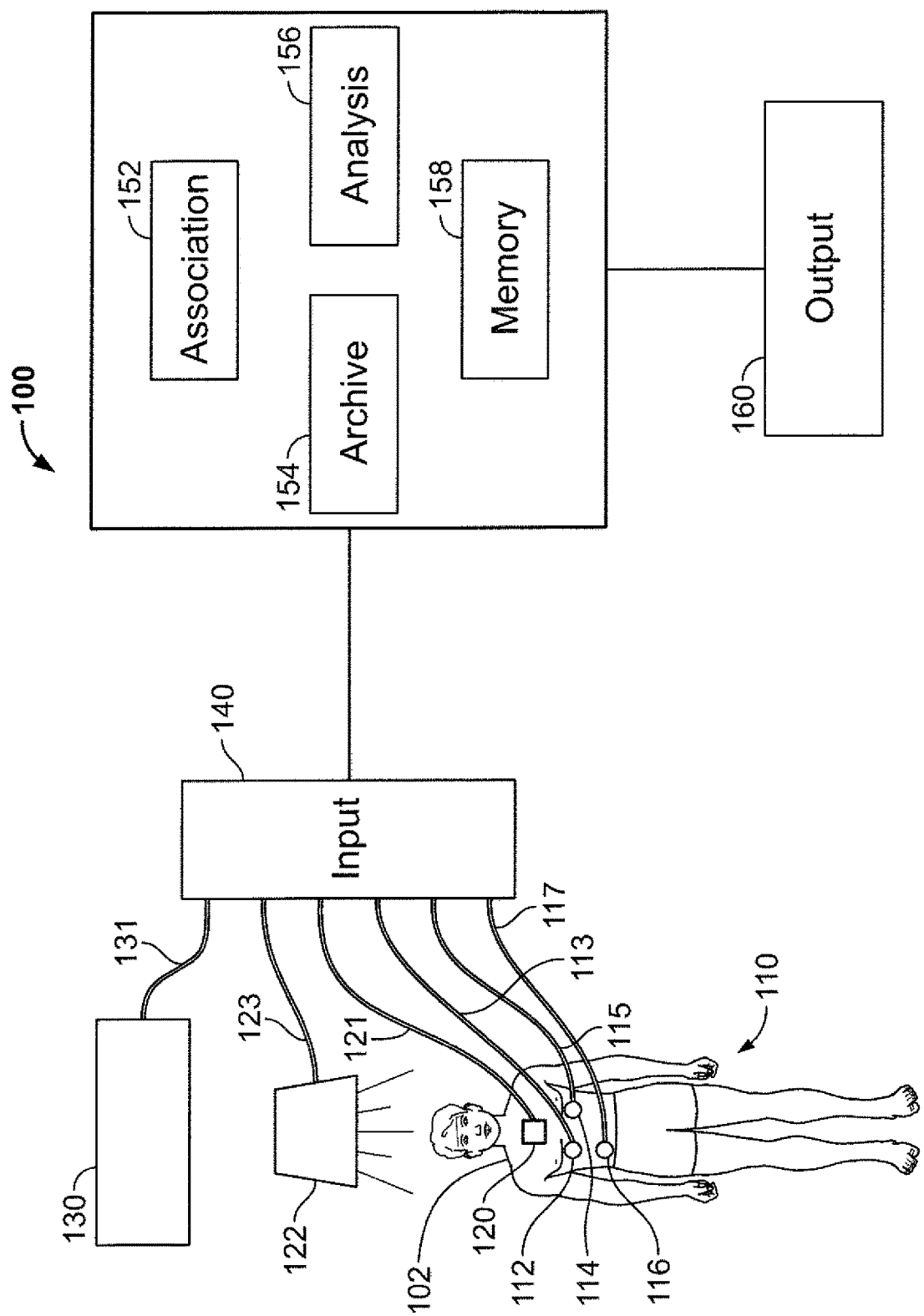
FIG. 1 is a schematic diagram of noise management system in accordance with various embodiments.

The following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or random access memory, hard disk, or the like) or multiple pieces of hardware. Similarly, the programs may be stand-alone programs, may be incorporated as subroutines in an operating system, may be functions in an installed software package, and the like. It should be understood that the various embodiments are not limited to the arrangements and instrumentality shown in the drawings.

As used herein, the terms "system," "unit," and "module" include a hardware and/or software system that operates to perform one or more functions. For example, a system, unit, or module may include electronic circuitry that includes and/or is coupled to one or more computer processors, controllers, or other logic based devices that perform operations based on instructions stored on a tangible and non-transitory computer readable storage medium, such as a computer memory. Alternatively or additionally, a system, unit, or module may include a hard-wired device that performs operations based on hard-wired logic of the device. The systems, units, or modules shown in the attached figures may represent the hardware that operates based on software or hardwired instructions, the software that directs hardware to perform the operations, or a combination thereof.

"Systems," "units," or "modules" may include or represent hardware and associated instructions (e.g., software stored on a tangible and non-transitory computer readable storage medium, such as a computer hard drive, ROM, RAM, or the like) that perform one or more operations described herein. The hardware may include electronic circuits that include and/or are connected to one or more logic-based devices, such as microprocessors, processors, controllers, or the like. These devices may be off-the-shelf devices that are appropriately programmed or instructed to perform operations described herein from the instructions described herein. Additionally or alternatively, one or more of these devices may be hard-wired with logic circuits to perform these operations. Further, "systems," "units," or "modules" may be configured to execute one or more algorithms to perform functions or operations described herein. The one or more algorithms may include aspects of embodiments disclosed herein, whether or not expressly identified in a flowchart or as a step of a method.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Various embodiments provide systems and/or methods for quantifying detected electrical noise events. The events may be quantified as the events relate to a patient at a point of capture of physiological and/or noise information. In various embodiments, the quantified information may be used for automated noise management. For example, use of a data set of noise information for a given event or patient visit, along with archived data sets from other events or patient visits, may allow improved visibility, awareness, or identification of repetitive or corresponding sequences, for example with respect to one or more of locations of data collection, operators performing data collection, equipment used to collect data, or the like. In various embodiments, the archived data may be used identify trip levels or thresholds for acceptable, tolerable, or permissible noise levels or other noise metrics, and automated alerts may be provided when a trip level or threshold exceeds a predetermined value.

In various embodiments, noise management or analysis may be approached as involving factual measurement and capture of information of a wide variety of types, including physiological measurements and interference or noise measurements, as well as environmental information such as time of collection, personnel involved in collection, collection techniques, and/or information describing the location at which the physiological measurements were made and/or equipment used. In various embodiments, correlation of such information for a number of events may be employed to improve consistency of collection and analysis of noise events. For example, types or sources of interference may be identified based on such correlations, with events providing similar data identified as corresponding to similar types or sources of interference. Alternatively or additionally, comparative or benchmark studies of personnel, equipment, and/or data collection techniques may be performed based on such correlations. Further alternatively or additionally, thresholds or limits may be established based on noise level metrics developed or identified using such correlations. The thresholds or limits may be used to alert personnel to potential problems with collected physiological data. By analyzing noise information across one or more of labs or locations, times of collection, personnel, or equipment used, more accurate diagnoses of cause of noise may be achieved.

Various embodiments provide novel techniques for noise management at one or more different levels, including data acquisition, data storage, and data analysis. For example, at an acquisition level, various embodiments provide for use of a separate recording channel for noise information, such as collected noise data and/or one or more noise metrics such as signal-to-noise ratio or quality of service, among others. The noise data channel may record data at a rate corresponding to a rate at which patient physiological information is obtained and/or recorded. For example, noise data on one or more noise channels may be collected at the same sample rate as physiological information collected for a patient, providing a 1:1 correlation of patient data to detected noise. In various embodiments, detected noise may be collected and stored on a single channel, or on multiple channels referenced at the same sample rate as physiological information or patient signals. In some embodiments, an environmental measure may be made on a sample per sample basis. A case noise profile may be provided from noise information for a given event, procedure, or patient visit using the collected noise information. In some embodiments, the case noise profile may also include physiological data stored on one or more physiological channels in addition to noise information stored on one or more noise channels.

Once noise information is collected, the noise information may be stored with collected physiological information and stored with a patient file, but not mixed with the physiological information to provide improved ease of extraction. Extracted noise data may be electronically transferred to a master data base maintaining an archive of noise cases or noise profiles. In addition to collected noise data (e.g., data acquired via a sensor configured to measure noise), environmental or other collection information may be associated with the collected noise data. Environmental or other collection information may include information regarding physician, medical team, or other personnel associated with the collection of the pertinent information; date and/or time of procedure or collection of information; physical location (e.g., address of building and/or location within building or other information identifying location of procedure or point of collection of information); equipment used (e.g., type of equipment and/or identification information for particular individual piece of equipment such as serial number, time of maintenance or replacement of equipment, time of installation or change of equipment); technique used for information collection; or the like.

Using standard data analytics or data analysis techniques, noise may be quantified in a variety of ways. For example, a relatively simple approach may note the duration and degree of interference of a particular case or event, the number of times noise exceeded a threshold (e.g., a user set threshold), and/or ratio of time during which noise (or noise above a given level) was experienced during a case relative to the total time of the case. These metrics may in turn be sampled and used as a detection flag to identify unacceptable thresholds. From these thresholds, alerts may be established to identify or highlight unacceptable label conditions and/or to identify or highlight data sets that are unacceptable based on one or more noise metrics.

In various embodiments, analysis of collected noise information may be used to determine if there are multiple unacceptable events or instances within a given case, or within a location under control of a given entity or operator. Analysis of correlated data as described herein may be performed to determine if one or more instances of noise or interference correspond to or are associated with a pattern involving one or more of location, personnel, equipment, or time. Further, analysis of correlated data may be performed to determine if noise is caused by an external source, such as interference from another part of a structure or nearby facility. With the cause or source of noise more accurately determined, the noise may be addressed and resolved more quickly, reliably, and/or inexpensively.

A technical effect of at least some embodiments provides automated data capture and analysis, and/or automated remediation or mitigation of noise or interference. A technical effect of at least some embodiments includes improved identification of causes of interference or noise. A technical effect of at least some embodiments provides automated noise profiling. A technical effect of at least some embodiments provides tailored or customized noise alert thresholds. A technical effect of at least some embodiments provides improved comparisons or benchmarking of personnel, equipment, and/or facilities with respect to noise or interference. A technical effect of at least some embodiments provides improved correlation of noise data over longer terms or time periods. A technical effect of at least some embodiments provides improved correlation of noise data with external or environmental factors or characteristics.

FIG. 1 provides a schematic diagram of a noise management system 100 in accordance with various embodiments. The noise management system 100 includes an input module 140, a processing unit 150, and an output module 160. The depicted input module 140 of the noise management system 100 receives information from a physiological sensor assembly 110, a first noise acquisition unit 120, a second noise acquisition unit 122, and an environmental information input module 130. In the illustrated embodiment, the physiological sensor assembly 110 acquires physiological data of a patient 102, and the first noise acquisition unit 120 and second noise acquisition unit 122 acquire noise information. The first noise acquisition unit 120 and the second noise acquisition unit 122 may acquire noise information simultaneously and/or concurrently with the acquisition of the physiological data. Information corresponding to the environment in which the physiological data and noise information are obtained is provided to the input unit 140 with the environmental information input module 130. The physiological data is recorded on at least one physiological channel of the processing unit 150, and the noise information is recorded on at least one noise channel of the processing unit 150. The noise information may be recorded at a sample rate corresponding to a rate used to record the physiological information.

The processing unit 150 is further configured to associate the noise information with the information provided by the environmental information input module 130 to provide a case noise profile for a particular procedure or patient visit of the patient 102. Thus, the case noise profile may include noise information obtained using the first noise acquisition unit 120 and second noise acquisition unit 122 (and/or derived from information obtained using the first noise acquisition unit 120 and second noise acquisition unit 122) and environmental information. Further still, in the illustrated embodiment, the processing unit 150 is configured to store the case noise profile as part of an archive. Archived case noise profiles may then be analyzed (e.g., using standard or conventional data analytic techniques) for a variety of purposes. For example, an individual case noise profile may be analyzed to determine if the noise present in the case noise profile is at or below an acceptable level, or if the physiological data associated with the case noise profile is not reliable due to an unacceptable noise level. As another example, a comparative study of environmental factors and/or the effects of environmental factors may be performed. For example, one or more of different locations at which physiological information was acquired, time at which physiological information was acquired, personnel acquiring physiological information, or equipment used to acquire physiological information may be evaluated. One or more of the locations, personnel, or equipment may be identified for remedial measures as part of the comparative study.

As yet another example, a case noise profile may be analyzed, using archived information, to identify a source or cause of noise (or likely source or cause of noise) in the collection of the physiological information associated with the case noise profile. For instance, noise profiles for cases for which one or more causes or sources of noise or interference are known may be stored and associated with the corresponding known causes or sources of noise or interference (which, for example, may be provided with a predetermined value for a parameter identifying the particular cause of interference). If a given case noise profile is analyzed and found to have a similar or comparable profile to a noise profile, group of noise profiles, or model or pattern noise profile having a known cause or source of noise, the given case may be correlated with or associated with the same cause or source of noise. For example, a number of cases which have been determined to be affected by a faulty lead may have a particular feature or aspect in a case noise profile. A subsequent case having a similar feature or aspect in its case noise profile may be identified as a case affected by (or likely to be affected by) a faulty lead and/or identified as a case for which the leads should be examined. As another example, noise from an outside source (such as a nearby building or facility) may result in a noise profile signature or pattern that may be identified by analyzing case noise profiles affected by such noise, with the signature or pattern identified using past case noise profiles used to troubleshoot or identify external noise sources in subsequent cases.

Thus, for example, a root cause of noise may be determined for previous cases or instances. For instance, operator observations and/or the results of investigations into the causes of noises may identify a cause of noise for a given case profile. As one example, an operator may notice that an electrode was improperly positioned and/or visibly damaged for a given case noise profile. A feedback mechanism may be provided by which, as a root cause (or causes) of noise is determined, the root cause (or causes) may be fed back into an archive system and associated with the appropriate case noise profile. Newly or subsequently acquired noise profiles may then be correlated with archived noise profiles that are already associated with a root cause of noise.

The depicted physiological sensor assembly 110 is operably connected to the body of the patient 102 and is configured to collect physiological information of the patient 102. In the illustrated embodiment, the physiological sensor assembly includes a first sensor 112, a second sensor 114, and a third sensor 116. The first sensor 112 is operably connected to the input unit 140 via a first data channel 113, the second sensor 114 is operably connected to the input unit 140 via a second data channel 115, and the third sensor 116 is operably connected to the input unit 140 via a third data channel 117. The data channels provide a path for data to travel from the detectors or sensors to the input module 140. For example, in the illustrated embodiment, the data channels are depicted as cables connecting the sensors and the input module 140. In the illustrated embodiment, the first sensor 112, second sensor 114, and third sensor 116 may be configured as electrodes attached to the chest or torso of the patient 102 and used in conjunction with three-lead electrocardiogram (ECG) detection.

It should be noted that the number and arrangement of sensors shown in FIG. 1 is provided for clarity of illustration and by way of example, and that other numbers, arrangements, and/or types of sensors may be employed in various embodiments. For example, 10 electrodes may be used as part of a 12 lead ECG system. As another example, a 15 lead ECG system may be employed in other embodiments. Additionally or alternatively, one or more pressure (e.g., blood pressure) sensors or detectors may be employed. Generally, the physiological sensor assembly 110 in various embodiments may include one or more sensors configured to sense any biometric physiological signal (or signals). As yet further examples, muscle waves or brain waves may be detected or sensed in various embodiments. For example, in various embodiments, detected physiological information may include measurement of one or more of an electroencephalogram (EEG), electroneurogram (ENG), electromyogram (EMG), or electroretinogram (ERG). The physiological data may be collected and/or recorded substantially continuously. As used herein, substantially continuous collection and/or recording of data or information may be understood as collection and/or recording at a relatively high sample rate (or a short interval between samples), for example at a rate corresponding to a highest practically available rate. For example, the physiological data may be collected or recorded substantially continuously at a sample rate within a range of about 1 kHz to about 4 kHz or higher. In some embodiments, lower sample rates 250 Hz and higher may also be utilized for these purposes.

In the illustrated embodiment, the noise management system 100 obtains noise information via two noise acquisition units, namely a first noise acquisition unit 120 and a second noise acquisition unit 122. The noise information may be collected contemporaneously and/or simultaneously with the physiological information. Further, the noise information may be collected at the same sample rate as the physiological information (e.g., at a rate with a range of between about 1 kHz and about 4 kHz), so that the noise information has a 1:1 correspondence with the physiological information. Thus, in various embodiments, noise readings may be time stamped and correlated 1:1 with physiological readings based on a collection time.

The first noise acquisition unit 120 is configured as a patient noise acquisition unit, and is configured to provide noise information to the input unit 140 and/or the processing unit 150 via a first noise data channel 121. The first noise data channel 121 may be configured, for example, as a cable communicably coupling the first noise acquisition unit 120 and the input unit 140. A patient noise acquisition unit as used herein may be understood as a noise acquisition unit configured to acquire noise via detection on or in a patient's body. A patient noise acquisition unit may be affixed to the body of a patient or inserted into the body of the patient. For example, the first noise acquisition unit 120 may measure a physiological signal or wave other than the physiological signal being measured by the physiological sensor assembly 110. For example, in embodiments where the physiological sensor assembly 110 measures brain waves, waves caused by the heart may be understood as noise relative to the brain waves. Thus, the first acquisition unit 120 may be used to measure cardiac waves as noise when the physiological sensor assembly 110 measures brain waves. In various embodiments, the first noise acquisition unit 120 may additionally or alternatively measure other sources of noise. For example, in embodiments where the physiological sensor assembly 110 measures cardiac waves utilizing multiple electrodes, a first noise acquisition unit 120 may be configured to measure a cumulative amount of noise and/or noise for each electrode (or for each lead) of the physiological sensor assembly 110. In some embodiments, all or a portion of the physiological sensor assembly 110 may be utilized as the first noise acquisition unit 120. For example, information or signals from the physiological sensor assembly 110 may be analyzed to obtain noise information. For example, physiological information (e.g., an ECG) may be compared to an expected and/or averaged ECG as part of a baseline analysis, with the difference between a measured ECG and the expected or average ECG analyzed as noise. Thus, in various embodiments, noise acquisition units may include a noise acquisition sensor and/or processing circuitry for analyzing information from other sensors (e.g., physiological sensor assembly 110).

The second noise acquisition unit 122 is disposed externally to the patient 102, and is configured to sense or detect noise or interference external of the patient 102, and to provide noise information to the input unit 140 and/or the processing unit via a second noise data channel 123. Thus, the depicted second noise acquisition unit 122 may be understood as an external noise acquisition unit. The second noise data channel 123 may be configured, for example, as a cable communicably coupling the second noise acquisition unit 122 and the input unit 140. The second noise acquisition 122 is configured to detect noise or interference from an area or volume surrounding and/or proximate to the patient 102 during collection of physiological data. For example, the second noise acquisition unit 122 may be positioned a distance from the patient 102, but within a room or lab in which physiological data is being collected from the patient 102. The second noise acquisition unit may be configured to detect electromagnetic interference (EMI). The second noise acquisition unit 122 may be configured to detect a level and/or a directionality of noise or interference. For example, the second noise acquisition unit 122 may be configured as an antenna. Additional details regarding noise acquisition units may be found in U.S. Pat. No. 8,515,530, "System and Method of Noise Detection in an Electrocardiology Study," issued Aug. 20, 2013, which is incorporated herein by reference in its entirety. Additionally or alternatively, the second noise acquisition unit 122 may be configured to detect or sense noise from one or more power supplies. For example, a second noise acquisition unit 122 may be configured to identify ground loop noise using readings taken at different locations.

In the illustrated embodiment, the environmental information input module 130 is configured to obtain environmental information and to provide environmental information to the input unit 140 and/or processing unit 150 via an environmental data channel 131. The environmental data channel may be configured, for example, as a cable communicably coupling the environmental information input module 130 and the input unit 140. Generally, the environmental data or information describes or corresponds to the physical and/or operational environment within which physiological data is collected by the physiological sensor assembly 110 at or near the time of collection. The environmental information obtained via the environmental information input module 130 may include information corresponding to an identification of a lab or facility used to collect physiological data, the location of the lab (e.g., geographic location and/or location of lab within a particular building or complex), nearby facilities and/or nearby potential sources of interference (e.g., train station, power lines, or the like), time of day, personnel used, technique used, equipment used, maintenance history of equipment used (e.g., new, refurbished, or the like).

In various embodiments, the environmental information input module 130 may be configured to obtain environmental information automatically (or autonomously), and/or via manual input from an operator. For example, an operator may input information identifying location of data collection, personnel involved in data collection, time of day and/or date of data collection, type and/or condition of equipment used to collect physiological data, positioning of equipment used to collect physiological data, or the like. The environmental information input module 130 may include one or more of a keyboard, keypad, mouse, touchscreen, or the like configured to receive input from an operator. Additionally or alternatively, environmental information may be provided automatically or autonomously to the input module 140 and/or the processing unit 150. For example, information from physiological sensors may be provided automatically with a time stamp identifying a time of acquisition. As another example, information from a physiological sensor may be provided with a header identifying a type of equipment or a serial number of equipment used to obtain physiological information. As yet one more example, an input module may be dedicated to or otherwise associated with a particular location, and may provide information identifying the lab or facility with which the input module is dedicated or associated.

Information obtained or acquired using the environmental information input module 130 may be associated with noise or interference information and used to provide a case noise profile. Various aspects of the environmental information may be parameterized, with numeric values of one or more parameters determined or assigned based on location, equipment, personnel or the like. Case noise profiles may be analyzed (e.g., using the processing unit 150) to develop analytic relationships between environmental conditions represented by or corresponding to the environmental information and detected or determined noise levels occurring during the collection of physiological data. For example, environmental information may be associated with noise information and correlated to identify an environmental source of noise or interference (e.g., a particular location associated with increased noise, a particular time associated with increased noise, a particular personnel group associated with increased noise, a particular type or piece of equipment associated with increased noise, or combinations thereof), and/or to compare or benchmark different times, locations, personnel, or the like.

The depicted input module 140 is configured to obtain physiological information from the physiological sensor assembly 110, noise information from the first noise acquisition unit 120 and the second noise acquisition unit 122, and environmental information from the environmental information input module 130, and to provide corresponding information to the processing unit 150. The information provided to the processing unit from the input module 140 may be raw (e.g., in the same form as received by the input module 140) and/or processed (e.g., one or more of converted from analog to digital, aggregated with similar noise, determined or derived from received information (for example, to provide a noise or quality of service metric), filtered, amplified, or provided with or converted to a parameterized value, among others). In some embodiments, the input module 140 may be configured to parameterize information received. For example, environmental information corresponding to locations, times, equipment, or the like may be assigned predetermined values distinguishing the various locations, times, or equipment. As another example, noise information may be organized based on a spectral analysis. For instance, noise levels at different portions of a spectrum may be identified and/or parameterized. It may be noted that, additionally or alternatively, processing of information received by the input module may be performed by the processing unit 150 and/or by a unit or module providing information to the input module 140.

Thus, the input module 140 may maintain information received via different data channels separately, or may combine or aggregate information. For example, for a multi-lead ECG system, the input module 140 may maintain information for each electrode separately and/or as an ECG determined using information from the electrodes. Similarly, noise information may be maintained separately or aggregated by the input module 140, and/or provided separately or aggregated to the processing unit 150. It may be noted that the input module 140 and the output module 160 are depicted as separate blocks in FIG. 1, but may be part of a combined physical unit in various embodiments. For example, in some embodiments, the processing unit 150 may include a touch screen that is utilized as an input unit and as an output unit. In various embodiments, the input module 140 may also be configured as a monitor configured to determine and/or display (e.g., via a screen or printout) physiological information, such as an ECG.

The depicted processing unit 150 is configured to receive, via the input module 140, information corresponding to physiological, noise or interference, and/or environmental information, to associate noise information with environmental information (and/or physiological information) to create a noise profile, and to store the case noise profile as part of an archive containing plural case noise profiles. The processing unit 150 may also be configured to one or more of identify analytic relationships between or among noise information, environmental information, and/or physiological information, perform studies of groups of case noise profiles (e.g., comparative studies), or analyze an individual case noise profile (e.g., to determine if the profile corresponds to an acceptable amount of noise or to identify a cause or causes of interference in the profile). It may be noted that the particular number and arrangement of processing units and/or modules shown in FIG. 1 is for illustrative purposes, and that other arrangements may be employed in other embodiments.

In the illustrated embodiment, the processing unit 150 includes an association module 152, an archive module 154, an analysis module 156, and a memory 158. The memory 158 may be configured as a tangible and non-transitory computer readable storage medium that is accessible to or utilized by one or more other modules or aspects of the processing unit 150. It may be noted that the particular number and arrangement of processing units and modules shown in FIG. 1 is for illustrative purposes, and that other arrangements may be employed in other embodiments. In various embodiments, the processing unit 150 may receive raw and/or processed information from the input module 140 (or from sensors or acquisition units). Received information may be processed, for example, by aggregating or combining, analyzing to determine a metric, filtering, amplifying, comparing to a threshold or the like.

Generally, in various embodiments, the processing unit 150 (and/or any sub-unit or module of the processing unit 150) may be understood as a processing circuitry unit and may include processing circuitry such as one or more field programmable gate array (FPGA), application specific integrated circuit (ASIC), integrated circuit (IC), or microprocessor. The processing unit 150 in various embodiments may be configured to execute one or more algorithms to perform functions or operations described herein. The one or more algorithms may include aspects of embodiments disclosed herein, whether or not expressly identified in a flowchart or as a step of a method.

Generally, in various embodiments, the processing unit 150 may be configured to develop individual case noise profiles, to archive case noise profiles, to develop models or other analytic relationships using the archived case noise profiles, and/or to utilize the models or analytic relationship to analyze individual case noise profiles or groups of case noise profiles. For example, archived case noise profiles may be used to identify patterns or signatures of causes of interference, and the identified patterns or signatures may be used to diagnose or identify a particular cause or causes of noise or interference for a given case noise profile (e.g., based on a level of similarity to one or more identified patterns or signatures).

The depicted association module 152 is configured to record received physiological information on at least one physiological recording channel and to record received noise information on at least one noise recording channel. Recording of the noise information and physiological information on different recording channels provides for easy and/or convenient extraction of noise information from physiological information, but still provides association of the information for analysis or study. For example, the noise information may be recorded at a sample rate corresponding to a sampling rate used to obtain the physiological information. Noise information received via different data channels may be recorded on separate noise recording channels, and/or may be combined or aggregated into an aggregate noise signal recorded on a noise recording channel. The recorded noise information may include at least one value of a noise metric (e.g., quality of service metric, signal to noise ratio, or the like), with the value of the noise metric determined by at least one of the input module 140 or the association module 152 based on information provided by the first noise acquisition unit 120 and/or the second noise acquisition unit 122.

The physiological information and the noise information may be recorded substantially continuously as described herein. Alternatively or additionally, noise information may be recorded at discrete intervals corresponding to a sampling rate of the physiological information. For example, the number of times one or more noise levels satisfies a threshold during a given period (e.g., number of physiological sample acquisition cycles) may be recorded. The association module 152 of the illustrated embodiment is also configured to associate the noise information with received environmental information to provide a case noise profile. For example, the noise information and environmental information for a given procedure, measurement, or patient visit may be stored as a first case noise profile, with noise and environmental information subsequent procedures, measurements, or patient visits used to provide subsequent case noise profiles.

In addition to association of environmental information additional information may be associated with the case noise profile and used to develop models or analytic relationships. For example, a known cause or causes of noise for a given case noise profile may be associated with the case noise profile. For instance, if a case noise profile is known to have been affected by a misplaced electrode, the case noise profile may include an indication of being affected by a misplaced electrode, and analyzed in conjunction with other case noise profiles known to be affected by a misplaced electrode to develop a pattern or model noise profile associated with a misplaced electrode. A case noise profile may also be associated with an indication whether or not the given case noise profile was affected by an acceptable or an unacceptable noise or interference level. The indications of, for example, a misplaced electrode or other cause of noise, or whether a level of noise is acceptable, may be provided as parameterized values to facilitate an analytic or mathematical analysis. Pattern or model profiles may be developed for acceptable and unacceptable noise levels, or as another example, for particular causes of interference or noise.

In various embodiments, the association module 152 may be configured to output a case noise profile to one or more additional systems for storage and/or further analysis. For example, one or more case noise profiles may be provided to a system health service or a remote service system. The system health service or remote service system may utilize received case noise profiles to identify a cause of noise to be addressed and/or to assess a system health of the system that acquired the physiological information associated with or corresponding to the case noise profile. It may be noted that in various embodiments one or more aspects of the association module 152 may be shared with or incorporated by the input module 140.

Figure 2:
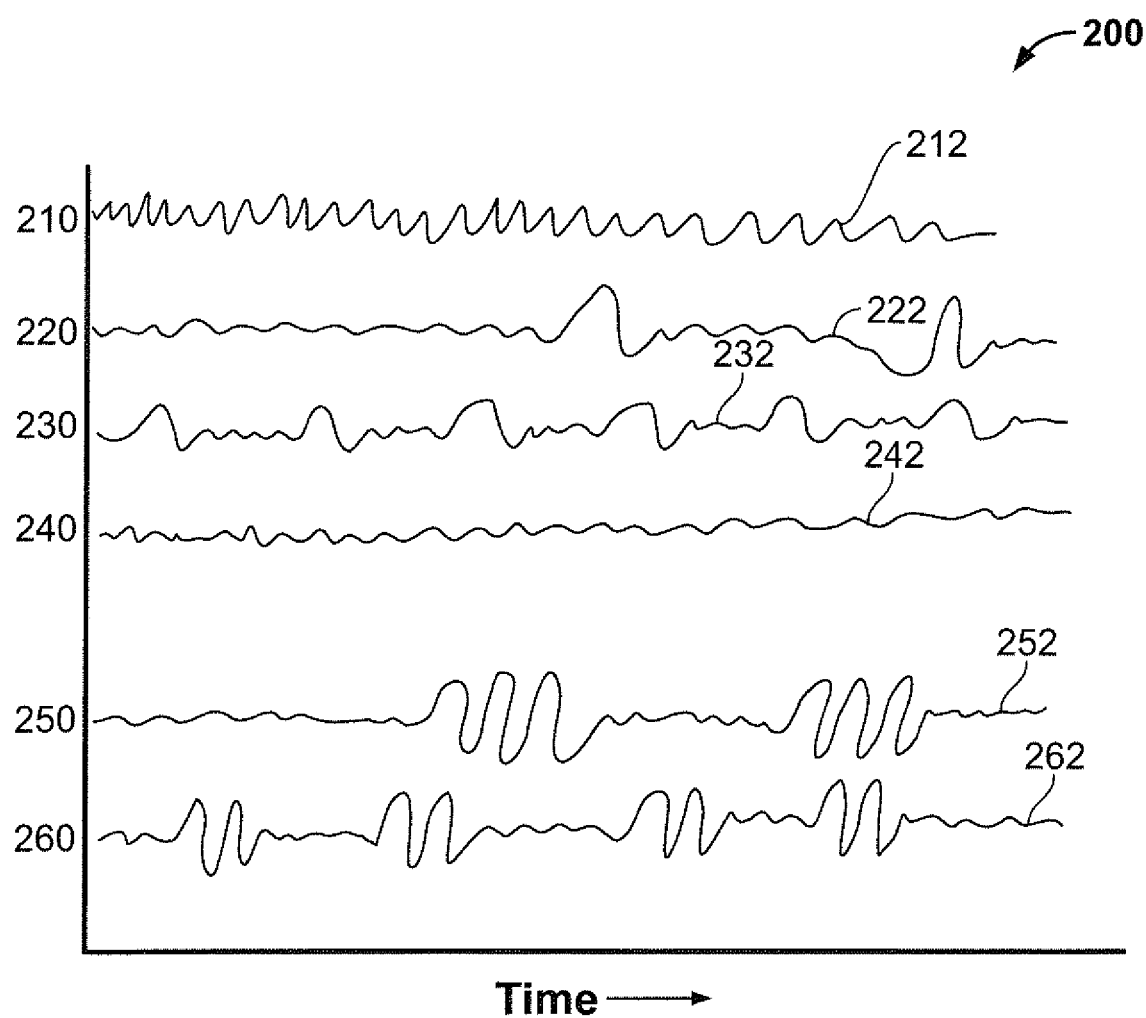
FIG. 2 illustrates recordings of physiological and noise information in accordance with various embodiments.

As mentioned above, the association module 152 may record various types of information on various recording channels. FIG. 2 illustrates a recording 200 of physiological and noise information in accordance with various embodiments. FIG. 2 provides an example of information from various sensors or acquisition units saved on corresponding dedicated recording channels. The recording 200 includes a first physiological signal 212 (e.g., information from a first physiological sensor 112) recorded on a first physiological recording channel 210. The recording also 200 includes a second physiological signal 222 (e.g., information from a second physiological sensor 114) recorded on a second physiological recording channel 220. Further, the recording 200 includes a third physiological signal 232 (e.g., information from a third physiological sensor 116) recorded on a third physiological recording channel 230. Finally, the recording 200 includes a fourth physiological signal 242

(e.g., information from an additional, fourth sensor) recorded on a fourth physiological channel 240.

The recording 200 also includes noise information recorded on noise recording channels. The depicted recording includes a first noise signal 252 (e.g., information obtained via the first noise acquisition unit 120) recorded on a first noise recording channel 250, and a second noise signal 262 (e.g., information obtained via the second noise acquisition unit 122) recorded on a second noise recording channel 260. As mentioned herein, the various noise signals may be obtained and/or recorded at a corresponding sample rate as the physiological signals. In the illustrated embodiment, the various physiological signals and noise signals are recorded substantially continuously at a 1:1 sampling rate compared to the other recorded signals.

In the embodiment depicted in FIG. 2, each recording channel records information from a single given sensor or acquisition unit. Also, in the embodiment depicted in FIG. 2, each recorded signal reflects an amplitude or level of a signal detected by a corresponding sensor or acquisition unit. In other embodiments, one or more determined metric and/or one or more combined or aggregated signal may be recorded. It may further be noted that environmental information may be recorded, stored, or otherwise associated with the recording 200 at a different sampling rate (or no sampling rate). For example, a start time, equipment identifier, personnel identifier, or location identifier may remain constant during collection of information, and thus a constant value for a given environmental parameter may be associated with a given case noise profile.

Figure 3:
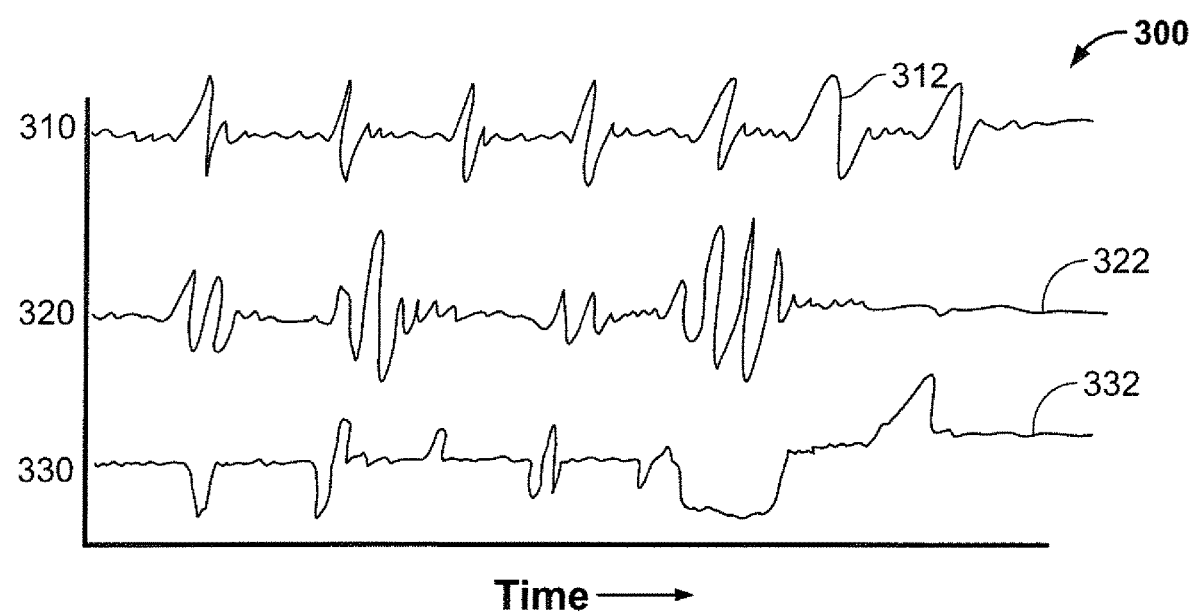
FIG. 3 illustrates recordings of physiological and noise information in accordance with various embodiments.

As mentioned above, in various embodiments, aggregate, combined, or determined information may be recorded on various recording channels. FIG. 3 illustrates a recording 300 of physiological and noise information in accordance with various embodiments which provide an example of aggregated signals. The recording 300 depicted in FIG. 3 includes an aggregate physiological signal 312 recorded on a physiological recording channel 310. The aggregate physiological signal 312 may be provided by a simple addition of physiological signals or a more complex combining or aggregating. For example, information from a plurality of electrodes may be analyzed to provide an ECG that is recorded on the physiological recording channel 310. The recording 300 also includes a first noise signal 322 recorded on a first noise recording channel 320. The first noise signal 322 in the illustrated embodiment is an aggregate noise signal. For example, the first noise signal 322 may be an aggregate of the first noise signal 252 and the second noise signal 262. Also, the recording 300 includes a second noise signal 332 recorded on a second noise recording channel 330. The second noise signal 332 may be a noise metric signal determined using noise information obtained via one or more noise acquisition units, and may be determined using physiological information as well. For example, the second noise signal 332 may represent a signal to noise ratio of the aggregate physiological signal 312 and the first noise signal 322.

Figure 4:
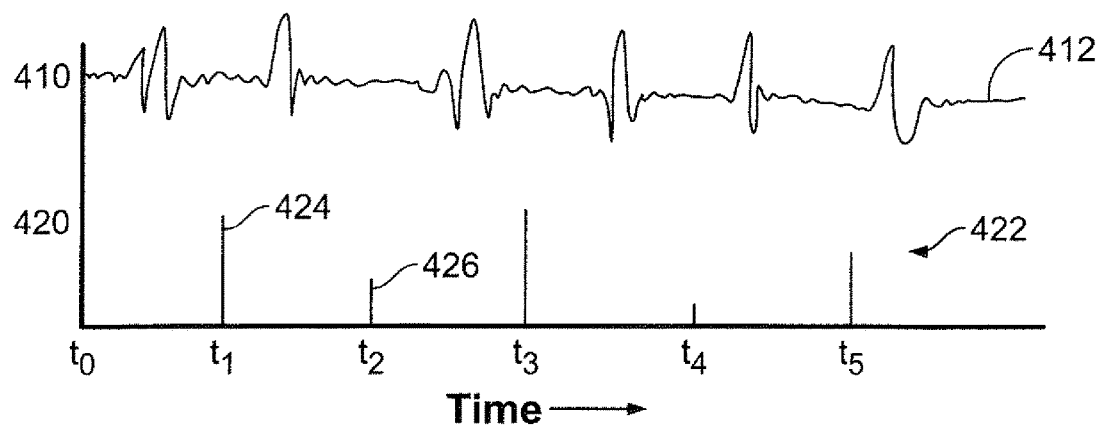
FIG. 4 illustrates recordings of physiological and noise information in accordance with various embodiments.

As mentioned above, noise information may be recorded at discrete intervals corresponding to the sample rate of the physiological information. For example, the number of noise readings meeting or exceeding a threshold over a given number of physiological samples may be counted and recorded on at least one noise recording channel. FIG. 4 illustrates a recording 400 of physiological and noise information including noise information recorded at discrete intervals in accordance with various embodiments. The recording 400 includes a physiological signal 412 (e.g., an ECG) recorded on a physiological recording channel 410. The recording 400 also includes a noise signal 422 recorded on a noise recording channel 420. The noise signal 422 represents the number of instances of noise levels satisfying a threshold over a given time period. For example, the number of instances from $t_0$ to $t_1$ is counted and recorded at a first record 424, the number of instances for $t_1$ to $t_2$ is counted and recorded at a second record 426, and so on. The interval between each counting and recorded may be based on a predetermined time period and/or number of samples for the physiological signal 412. It may be noted that, in various embodiments, noise metrics may be developed, using acquired noise information by one or more noise acquisition units, by one or more of the input module 140, association module 152, or analysis module 156.

It should be noted that the particular number, form, type, and combination of signals and recording channels in FIGS. 2-4 are provided by way of example for illustrative purposes. Other numbers or types of channels and signals may be utilized in various embodiments.

Returning to FIG. 1, recorded and associated information from the association module 152 is provided to the archive module 154 and the analysis module 156. For example, the depicted archive module 154 receives information (e.g., a case noise profile including noise information associated with environmental information (which may be parameterized)) from the association module 152 (and/or analysis module 156). The archive module 154 is configured to store a received case noise profile as part of an archive containing plural case noise profiles. The archived case noise profiles may be analyzed (e.g., using parameterized values and conventional data analytic techniques) to develop or identify relationships between causes of interference and noise profiles and/or to identify trends in collected data. For example, patterns or signatures for a causes or sources of interference may be developed (by the archive module 154 and/or the analysis module 156) and stored in the archive module 154. For instance, a first pattern or signature may be identified that corresponds to a misplaced electrode. A second pattern or signature may be identified that corresponds to a malfunctioning electrode. A third pattern or signature may be identified that corresponds to excessive interference from a ground loop of a power supply. Then, subsequently acquired case noise profiles that are analyzed and found to match one of the patterns or signatures may be identified as being affected by or likely to be affected by the corresponding cause. For example, a case noise profile matching the third pattern or signature may be identified as being affected by excessive interference from a power supply, and/or a power supply at a location where the given case noise profile was obtained may be identified for further investigation and/or repair. It may be noted that the archive module 154 may be part of an integral unit with one or more other aspects of the processing unit 150, or may be disposed at a remote location and connected wirelessly, via an interne, or the like.

In the illustrated embodiment, the analysis module 156 is configured to receive information (e.g., a case noise profile including noise information and associated environmental information) from the association module 152, and to analyze the case noise profile. The analysis module 156 may also be configured to analyze a group of case noise profiles obtained via the archive module 154. For example, the analysis module 156 may be configured to analyze the case noise profiles stored in the archive module 154 to develop analytic relationships or models used for analyzing subsequently obtained case noise profiles (e.g., to identify causes of interference, to determine if a noise level is acceptable).

The developed analytic relationships may be universal or determined across a relatively large group of locations, personnel, or equipment, or may be tailored to a particular group of locations, personnel, equipment, or combination thereof. The analytic relationships may be developed using conventional numeric techniques such as simulated annealing or random walk algorithms, among others. For example, minima and maxima of an obtained case noise profile may be examined to identify a best fit among model or pattern profiles, with attributes of the model or pattern (e.g., acceptability, unacceptability, identification of a cause or causes of noise) associated with the model attributed to the obtained case noise profile. For example, a case noise profile determined to closely match a pattern or signature corresponding to a faulty electrode may be determined to have a faulty electrode associated therewith. The analytic relationships may be configured as mathematical relationships in n-space with n parameters, with parameters including for example, information from predetermined spectral frequency ranges (e.g., every 25 Hz) and parameterized environmental information (e.g., a given value for a particular location, another given value for a particular operator or personnel group, another given value for a type of equipment, and the like).

In various embodiments, the analysis module 156 may be configured to perforin a comparative study of plural locations from which at least some of the case noise profiles have been obtained, including identifying at least location for remedial measures. For example, a location may be identified that suffers from a relatively large amount of noise levels and/or unusable data. The identified location may be studied or investigated further (either analytically or on-site) to help determine and remedy any causes of undue interference. Additionally or alternatively, groups of personnel, equipment, or times of data collection may be studied as part of a comparative study. Environmental factors (e.g., location, personnel, equipment used, or the like) that suffer from high noise levels may be identified for remedial measures, while environmental factors that have relatively low noise may be studied further to identify effective data collection techniques, for example used to train personnel and/or design labs or data collection facilities.

As another example, in various embodiments, the analysis module 156 may be configured to identify a source of noise for a case noise profiles, for example based on models, patterns, signatures, or analytic relationships developed using an archive of case noise profiles. As one more example, the analysis module 154 may be configured to perform an analysis of a given case noise profile to determine if the case noise profile represents an acceptable amount of noise based on whether the case noise profile (e.g., a noise metric included in the case noise profile or determined using the case noise profile) satisfies a threshold. The threshold may be developed or identified based on information regarding archived case noise profiles (e.g., previously obtained case noise profiles identified as either acceptable or unacceptable). The analysis module 154 may be used to analyze groups of case noise profiles to identify trends regarding noise levels for locations, personnel, or the like. For example, analysis of a number of case noise profiles may indicate a high noise level or issue re-occurring at a given location at a particular time of day. The location may then be investigated at the particular time of day, improving the chances of quickly and accurately identifying the cause of noise.

The output module 160 is configured to receive information from one or more of the input module 140 or the processing unit 150 (or module or aspect thereof) and to provide a display to an operator. In various embodiments, the output module 160 may display one or more of a noise level, a noise metric, an alert, an alert with prompt, a prompt to assist with entry of environmental information, or physiological information or signal (e.g., ECG). For example, the output module 160 may include a screen and/or printer for providing a display. The output module 160, in various embodiments, may be configured to provide an alert (one or more of audibly or visually) indicating an unacceptable amount of noise. For example, a case noise profile for information being collected during a given patient visit may be analyzed during or shortly after data collection and determined to be acceptable or unacceptably during the patient visit. If the noise is unacceptable, the output module 160 may provide a prompt to an operator to re-obtain the physiological data. If the cause or causes of interference are identified (e.g., by the analysis module 156), a prompt describing the cause or likely cause of interference may be provided to the operator, allowing the operator to remedy and/or investigate the identified cause. For example, if, during or shortly after the collection of physiological information during a patient visit, a case noise profile for the patient visit is identified as being adversely affected by a particular cause of interference, a prompt describing the cause of interference may be provided to the operator. The cause of interference may then be addressed during the same patient visit and more reliable physiological information obtained after addressing the cause of interference, without requiring a subsequent patient visit, thereby reducing the cost and/or inconvenience of a follow-up visit to acquire physiological information of an acceptable quality.

Figure 5:
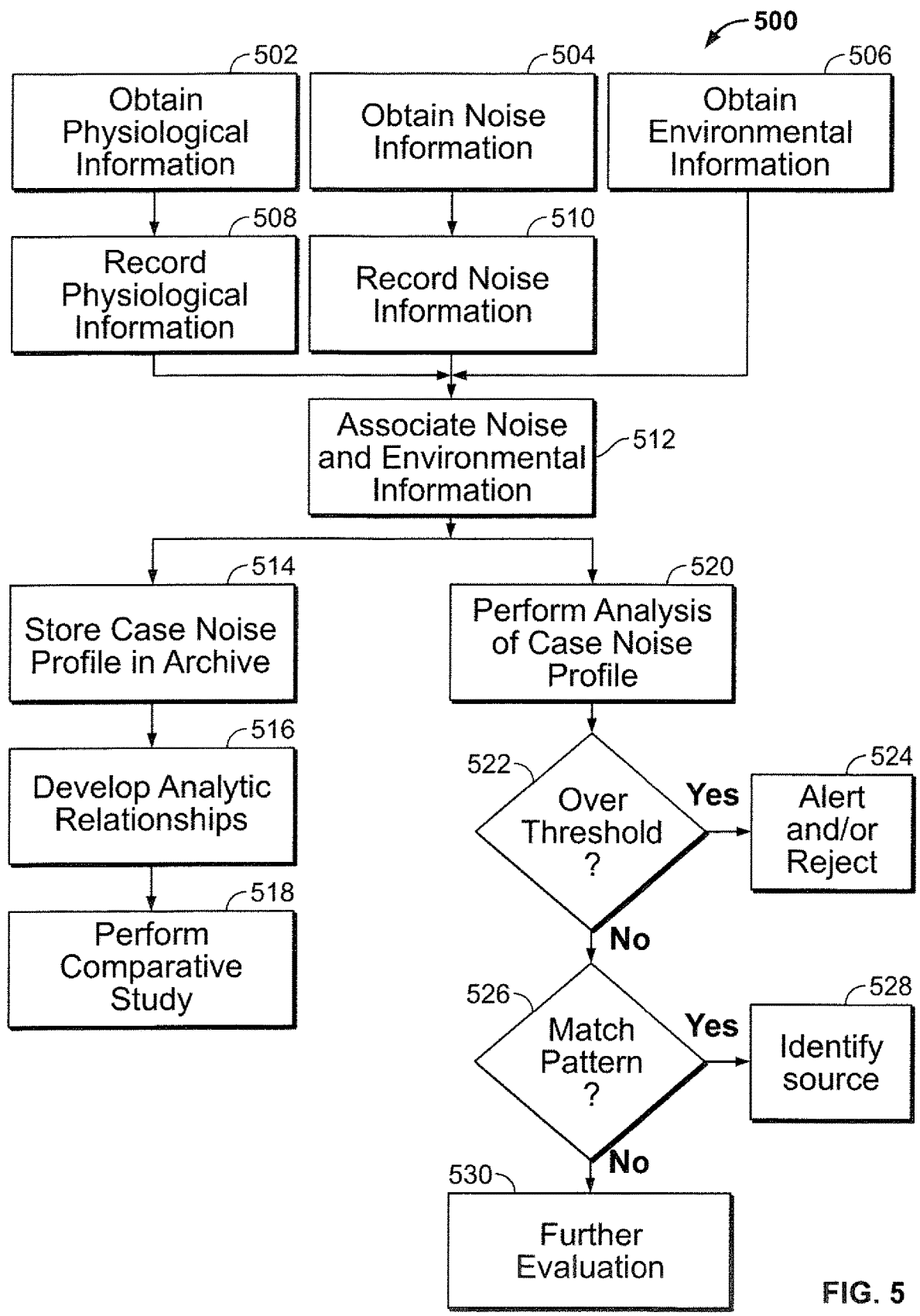
FIG. 5 is a flowchart of a method for noise management in accordance with various embodiments.

FIG. 5 provides a flowchart of a method 500 for noise or interference management in accordance with various embodiments. The method 500, for example, may employ or be performed by structures or aspects of various embodiments (e.g., systems and/or methods) discussed herein. In various embodiments, certain steps may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. In various embodiments, portions, aspects, and/or variations of the method 500 may be able to be used as one or more algorithms to direct hardware to perform one or more operations described herein. For example, one or more aspects of the method 500 may be performed automatically or autonomously (e.g., without operator interference) by one or more processing units as described herein (e.g., processing unit 150).

At 502, physiological information is obtained. For example, the physiological information may be obtained from a patient using at least one physiological sensor. In various embodiments, the at least one physiological sensor may include one or more electrodes or leads configured for measurement of cardiac waves and to provide an ECG. Additionally or alternatively, the physiological information may correspond to a pressure (e.g., blood pressure). In some embodiments, the physiological information may correspond to a brain wave or muscle wave. In various embodiments, the at least one physiological sensor used to obtain the physiological information may include one or more sensors configured to sense any biometric physiological signal (or signals).

At 504, noise information is obtained. The noise information may be obtained using at least one noise acquisition unit (e.g., first noise acquisition unit 120, second noise acquisition unit 122). The noise information corresponds to noise or interference occurring during collection of the physiological information. Noise may occur during collection of physiological information due to one or more causes. For example, noise or interference may be provided by a surrounding environment (e.g., a nearby facility or equipment), a fault or defect in collection equipment (e.g., a malfunctioning or improperly positioned sensor or lead), or internal sources of a patient (e.g., a signal other than the signal desired to be measured), among others. The noise information may include a noise metric, such as signal to noise ratio, for example. Thus, in some embodiments, a value of a noise metric may be determined using data detected by at least one noise acquisition unit. For example, one or more noise signals may be compared to one or more physiological signals to determine a noise metric (e.g., signal to noise ratio). It may be noted that a physiological sensor may be utilized to obtain noise information in some embodiments. As one example, a given physiological signal (e.g., ECG) may be considered as noise when a different physiological signal (e.g., brain wave) is being measured. As another example, noise information may be obtained from a physiological signal. For instance, a determined ECG signal (e.g., an expected signal or a signal determined from plural ECG cycles, for example an averaged ECG signal) may be subtracted from an obtained ECG signal to provide a baseline signal from which a noise signal may be determined.

At 506, environmental information is obtained. The environmental information may correspond to at least one of a time or location at which the physiological information was acquired from the patient. In various embodiments, the environmental information may include information corresponding to or describing the time of collection, personnel involved in collection, collection techniques, or the location at which the physiological measurements were made and/or equipment used, among others. For example, the type of equipment, condition of equipment (e.g., new, properly functioning, improperly functioning, damaged, recently repaired, time since maintenance or repair, previously documented malfunctions) and position of equipment may be included with the environmental information. As another example, an identification of the location (e.g., particular lab at which data is collected) may be included with the environmental information. The environmental information may be provided manually via an operator entry and/or automatically. For example, in some embodiments, an input module (e.g., environmental information input module 130) may be utilized by an operator to manually enter (e.g., via a touch screen or keyboard, among others). Additionally or alternatively, the environmental information may be automatically or autonomously provided. For example, a physiological sensor and/or input module may automatically provide information identifying the physiological sensor or type of physiological sensor, with the information provided in a header of a message or signal providing the physiological information. As another example, a time stamp may be autonomously provided by an input unit. As yet another example, an input unit or data collection device may be associated with or dedicated to a particular physical location (e.g., identification of a particular lab at which physiological data is collected), and data provided by the input unit or data collection device may be automatically recognized as being from the particular physical location.

At 508, the physiological information is recorded. The physiological information may be recorded on at least one physiological channel. For example, each physiological sensor may have information therefrom recorded separately on a dedicated physiological recording channel. As another example, two or more physiological sensors may have information therefrom combined or aggregated on a physiological recording channel. For instance, information from ten electrodes may be variously combined and recorded on plural channels in connection with a twelve lead ECG measurement. The physiological information may be recorded at a relatively high sample rate, and may be recorded substantially continuously as described herein. For example, the physiological information may be recorded at a sample rate between about 1 to about 4 kHz (or higher) in various embodiments. As another example, the physiological information may be recorded at about 250 Hz and higher in various embodiments.

At 510, the noise information is recorded on at least one noise recording channel. In various embodiments, the noise information may be recorded at a sample rate corresponding to the sample rate used to record the physiological information. For example, the noise information may be obtained or recorded at a shared or common sample rate as the physiological information. In some embodiments, the noise and physiological information may be recorded substantially continuously. For example, the noise and physiological information may be recorded at a common sample rate between about 1 kHz and about 4 kHz (or higher). Alternatively or additionally, noise information may be recorded at discrete intervals corresponding to the sample rate of the physiological information. For example, the number of noise readings meeting or exceeding a threshold over a given number of physiological samples may be counted and recorded on at least one noise recording channel. Further, in some embodiments, an aggregate or combined noise signal using information obtained via plural noise acquisition units may be recorded on a noise recording channel. In some embodiments, the noise information may be recorded on plural noise recording channels. As one example, noise information from plural noise acquisition units may be recorded on separate, dedicated noise recording channels. As another example, raw or unprocessed noise information from one or more noise acquisition units may be recorded on a corresponding noise recording channel or channels, and a noise metric (e.g., a signal to noise ration) may be recorded on a different noise recording channel. As described herein, the noise information may be obtained from one or more noise acquisition units, and may be recorded in a raw or unprocessed form as received from a noise acquisition unit, or may be recorded in a processed form. For example, the noise information may be processed to provide a noise metric such as signal to noise ratio that may be recorded on a noise recording channel.

At 512, noise information (e.g., information obtained at 504 and/or recorded at 512) and environmental information (e.g., information obtained at 506) are associated. In various embodiments, the noise and environmental information are associated to provide a case noise profile for a particular patient, examination, and/or hospital or clinic visit. For example, noise information (e.g., noise data recorded on one or more noise recording channels and/or noise metrics obtained from such noise data) from a particular patient visit to a given facility at a given time or time period may be saved as part of a case noise profile along with environmental information (such as time of collection, personnel, lab or facility used to collect data, or equipment used to collect data, among others). In various embodiments, alternatively or additionally, physiological information may be associated with noise information. For example, physiological information and noise information recorded at a common sample rate may be associated and saved on a 1:1 sample basis.

It may be noted that in various embodiments the noise information may be associated with but not mixed with the physiological information (e.g., the noise information may not be combined with the physiological information, but may instead be stored on separate recording channels) to provide for easier extraction of noise information from physiological information. Further still, noise information may be associated with a known cause or source of interference. For example, if it is known that a given noise profile was obtained with a defective ECG electrode or lead, the noise profile may be stored with a notation or other identifier indicating that the noise profile was obtained with a defective ECG electrode or lead. As another example, if interference from a particular external source (e.g., passing train or interference from nearby lab or facility, among others) is known to have occurred during collection of the information for the case noise profile, the case noise profile may be stored with a corresponding notation or other identifier. In some embodiments, if a cause or source of interference is not known at an initial time, the case noise profile may be stored without an associated cause or source; however, if the cause or source of interference is later determined, the case noise profile may be updated to be associated with the cause or source of interference. The associated cause or source may be used to help identify environmental causes or source of interference for subsequently obtained case noise profiles that are similar in one or more respects. Alternatively or additionally, a case noise profile may be associated with an identifier indicating whether or not the case noise profile corresponds to an acceptable noise or interference level or not.

At 514, the case noise profile is stored in an archive. The case noise profile in various embodiments may be stored with or without corresponding physiological information. The archive may contain plural case noise profiles, from which relationships (e.g., parametric relationships) or other models for analyzing subsequently obtained case noise profiles may be built. Parameters used in such relationships may include or represent, for example, noise levels (e.g., noise levels at different frequencies across a spectrum), noise metrics (e.g., signal to noise ratio), or environmental aspects (personnel, time of collection, location of collection, equipment used, or the like).

At 516, one or more analytic relationships are developed. The one or more analytic relationships may be developed based on the case noise profiles stored in the archive. As the number of case noise profiles stored in the archive increase, the analytic relationships may become more refined, for example more detailed, complex, and/or reliable. The analytic relationships may be updated as case noise profiles are added to the archive. The analytic relationships may be parametric or other types of models. For example, the analytic relationships may be built using case noise profiles having known associated causes or sources of interference or noise, with particular patterns or signatures for each cause or source of interference defined by the analytic relationships. For instance, a first pattern or signature may be determined for a first cause of noise, such as improper electrode placement. A second pattern or signature may be determined for a second cause of noise, such as a damaged or malfunctioning lead or electrode. A third pattern or signature may be determined for a third cause of noise, such as interference from a nearby scanning facility. Additional patterns or signatures may be determined for additional causes or sources of noise. Newly acquired case noise profiles may be correlated with archived case noise profiles already associated with an identified cause or source of noise. In some embodiments, for subsequently obtained case noise profiles with unknown causes of noise, a closely matching pattern or signature (e.g., within a predetermined margin or difference) for an identified source of noise may be identified, and the identified source of noise determined to be the cause or source of noise (or likely source or cause of noise) for the subsequently obtained case noise profile.

In one example scenario, a case noise profile is obtained, and various parameters defined by the case noise profile are determined to substantially match a pattern or signature previously determined to match case noise profiles obtained with an improperly placed electrode. The case noise profile may be identified as having been obtained with an improperly placed electrode and/or may be identified for further investigation regarding the placement of electrodes. Alternatively or additionally, analytic relationships may be developed to provide a threshold or other identifier for acceptable quality. For example, a threshold of a given metric or group of metrics may be determined based on archived case noise profiles that are known to correspond to acceptable or unacceptable noise or interference levels. As another example, a parametric model may be employed, with certain patterns or signatures corresponding to acceptable noise levels and other patterns or signatures corresponding to unacceptable noise levels. In various embodiments, case noise profiles may be analyzed using one or more multi-dimensional optimization algorithms utilizing minima and maxima to optimize fit. In some embodiments, physiological information may be used in developing and/or applying the analytic relationships, while in other embodiments physiological information may not be employed.

At 518, a comparative study is performed. The comparative study may be performed to identify difference in noise levels across different locations, equipment, personnel, or the like. The comparative study may identify one or more of personnel, location, or equipment associated with lower quality (e.g., higher noise or interference) data collection, and/or may identify one or more of personnel, location, or equipment associated with higher quality (e.g., lower noise or interference). In various embodiments, the comparative study may be of plural locations from which at least some of the case noise profiles in an archive have been obtained. The comparative study may be performed using the plural case noise profiles and may include identifying at least one location for remedial measures. For example, case noise profiles in an archive may be employed to develop measures of noise effectiveness or efficiency. Then, case noise profiles for different locations, different times, different personnel, and/or different equipment may be analyzed and compared. Thus, for example, locations, equipment and/or personnel associated with poor noise levels may be identified for remedial measures. For example, a location (e.g., lab) may be identified for further investigation. As another example, if a particular time provides worse noise levels than other times, the particular time may be investigated further and/or avoided for data collection. As another example, a piece of equipment associated with higher noise levels may be identified and repaired or replaced. As still another example, personnel associated with higher noise levels may be provided with additional training. Further, for example, personnel associated with lower noise levels may be studied to identify techniques to reduce noise levels and/or may be utilized to train personnel associated with higher noise levels. Further, combinations of equipment, personnel, time, and location (among others) may also be studied, and trends may be determined using the archive of case noise profiles. For example, a trend of better (or worse) noise levels may be identified at a given location at a particular time, or, as another example, with given personnel at a particular location. By determining more specifically combinations of time, location, equipment, and/or personnel, a cause or source of interference or noise may be identified more quickly and reliably, and appropriate remedial measures may be instituted more quickly. In various embodiments, using analytic relationships developed based on archived case noise profiles may reduce or eliminate costly and/or time consuming on-site investigations and identify and mitigate causes of noise or interference more quickly, reliably, and/or cost-effectively.

At 520, an analysis of the case noise profile (e.g., a case noise profile obtained at 512) is performed. The analysis may be performed using one or more analytic relationships or models developed using archived case noise profiles. For example, for a given case noise profile, similar noise profiles (e.g., having a similar pattern or signature as defined by a parametric relationship) may be located in an archive based on local maxima and minima of one or more n-space parametric relationships. Or, as another example, a standard or base profile for a given condition (e.g., cause or source of noise or interference) may be developed and a subsequently acquired case noise profile compared to the standard or base profile. If the acquired case noise profile is sufficiently similar to the standard or base profile, the acquired case noise profile may be determined to have a similar cause or source of noise as the standard or base profile. As another example, a threshold or acceptable noise measure (e.g., noise level, metric, pattern, signature) may be determined based on archived case noise profiles, and an acquired case noise profile analyzed to determine whether or not the acquired case noise profile satisfies the threshold or acceptable noise measure.

At 522, it is determined if one or more noise metrics of the case noise profile are over a threshold or acceptable level. For example, the number and/or frequency of occurrences of noise (or noise metric such as signal to noise ratio) above a given value may be used to determine if the case noise profile defines an acceptable amount of noise, and if corresponding physiological data should be discarded. In various embodiments, noise may be quantified by one or more of the duration of interference for a case, the degree of interference for a case, the number of times noise exceeded a predetermined threshold, or total case time to noise time for the case. These metrics may in turn be sampled and used as a detection flag to identify unacceptable thresholds. If the noise or interference for the case noise profile exceeds the threshold, the method 500 proceeds to 524. If not, the method proceeds to 526.

At 524, if the noise or interference for the case noise profile was over the threshold, an alert is provided for the case noise profile and/or the case noise profile is rejected. For example, an operator collecting physiological data corresponding to the case noise profile may be alerted that the collected data includes an unacceptable amount of noise, and that a new set of physiological data should be collected. If a source or cause of the noise or interference of the noise in the case noise profile may be identified based on analytic relationships (e.g., analytic relationships developed using an archive of case noise profiles), the alert may also include an identification of the sources or causes of noise (or likely sources or causes of noise). For example, in one example scenario, the case noise profile for a set of data currently or recently acquired defines a parametric relationship (e.g., signature or pattern) that matches a corresponding signature or pattern previously identified or associated with a misplaced electrode. The alert provided to an operator may then indicate that additional data should be collected, and that the placement of all electrodes should be checked before collecting additional data. Thus, in various embodiments, depending on an identified source (or likely or potential source) of interference, an operator may be provided with a prompt indicating one or more remedial steps that may be taken to address an identified source of interference.

At 526, it is determined if the case noise profile matches a pattern. For example, information in the case noise profile may match a pattern or signature corresponding to or associated with a particular cause or causes of noise as determined from an analysis of archived case noise profiles. A profile may be understood as matching a pattern in various embodiments based on an amount or degree of similarity of local maxima or minima of a parametric relationship. For example, a particular pattern of increased incidences of exceeding a threshold at a frequency or group of frequencies as part of a spectral analysis may indicate one or more potential causes or sources of interference. If the case noise profile matches a pattern or signature, the method 500 proceeds to 528. If not, the method 500 proceeds to 530.

At 528, the source of noise or interference is determined based on the matched pattern. In various embodiments, the identified source may be a likely or possible determination that is verified or confirmed using further analysis. In some embodiments, more than one potential source of interference may be identified based on a pattern or signature of a case noise profile. A particular cause may then be determined either using further analytics, or by a determination by an operator. For example, a list of potential causes of noise or interference may be presented to an operator, who may then inspect the equipment and/or location at which data is being collected to determine which of the causes of noise may be applicable to a given case.

At 530, further evaluation is performed. For example, if an unacceptable amount or level of noise is determined, but no previously modeled source or cause of noise from an archive sufficiently matches a signature or pattern of the case noise profile, the closes match may be examined to see if the corresponding cause or source of noise or interference applies. Further, a given case noise profile may be used to update or modify one or more previously defined patterns or signatures in an archive. Further still, a case noise profile may be examined for consistency or inconsistency with a trend of results for a given location, equipment, personnel, and/or time of data collection. For example, if a given case noise profile corresponds to an unacceptable amount of noise, but other recent case noise profiles for the same location and personnel correspond to acceptable noise levels, the time of data collection and/or equipment used may be identified for further analysis or investigation. In various embodiments, further analysis of case noise profiles may be used to determine whether there are multiple unacceptable events within a group of cases. (It may be noted that such an analysis may also be performed in connection with step 518 discussed herein.) The determination may be made autonomously in some embodiments, (e.g., via an analysis module 156 and/or a processing unit 150), while in other embodiments a list of events and/or identified causes of events may be provided to an operator (e.g., lab manager or administrator). In some embodiments, a correlation analysis or comparative study may be performed on the identified case noise profiles to determine if the events conform to a pattern relative to personnel, location, equipment, and/or time. The correlation analysis or comparative study may help establish, for example, if there are staff training or equipment issues, or, as another example, if the events have an external cause.

It should be noted that the particular arrangement of components (e.g., the number, types, placement, or the like) of the illustrated embodiments may be modified in various alternate embodiments. In various embodiments, different numbers of a given module or unit may be employed, a different type or types of a given module or unit may be employed, a number of modules or units (or aspects thereof) may be combined, a given module or unit may be divided into plural modules (or sub-modules) or units (or sub-units), a given module or unit may be added, or a given module or unit may be omitted.

It should be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid state drive, optical drive, and the like. The storage device may also be other similar means for loading computer programs or other instructions into the computer or processor.

As used herein, the term "computer," "controller," and "module" may each include any processor-based or microprocessor-based system including systems using microcontrollers, reduced instruction set computers (RISC), application specific integrated circuits (ASICs), logic circuits, GPUs, FPGAs, and any other circuitry capable of executing the functions described herein. The above examples are exemplary only, and are thus not intended to limit in any way the definition and/or meaning of the term "module" or "computer."

The computer, module, or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer, module, or processor as a processing machine to perform specific operations such as the methods and processes of the various embodiments described and/or illustrated herein. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program. The individual components of the various embodiments may be virtualized and hosted by a cloud type computational environment, for example to allow for dynamic allocation of computational power, without requiring the user concerning the location, configuration, and/or specific hardware of the computer system It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the invention without departing from their scope. While the dimensions and types of materials described herein are intended to define the parameters of the various embodiments of the invention, the embodiments are by no means limiting and are exemplary embodiments. Many other embodiments will be apparent to those of skill in the art upon reviewing the above description. The scope of the various embodiments of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure.

This written description uses examples to disclose the various embodiments of the invention, and also to enable any person skilled in the art to practice the various embodiments of the invention, including making and using any devices or systems and performing any incorporated methods. The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal language of the claims.

What is claimed is:
1. A method comprising:
   obtaining, via at least one physiological sensor, physiological information of a patient, wherein the physiological information is acquired autonomously with the at least one physiological sensor;
   acquiring environmental information corresponding to at least one of a time or location at which the physiological cal information was obtained;
   obtaining, via a noise acquisition unit, noise information corresponding to electronic noise occurring during col- lection of the physiological information, wherein the noise information is acquired autonomously with the noise acquisition unit;
recording the physiological information on at least one physiological recording channel;
recording the noise information on at least one noise recording channel at a sample rate corresponding to a sample rate used to record the physiological information;
associating, with at least one processor, the noise information with the environmental information to provide a case noise profile that includes the physiological information, noise information, and environmental information, wherein the noise information and physiological information are associated without being mixed in the case noise profile; and
storing the case noise profile as part of an archive containing plural case noise profiles, wherein the case noise profile that is stored as part of the archive includes both the noise information and the physiological information.

2. The method of claim 1, further comprising performing, with at least one processing unit, a comparative study of plural locations from which at least some of the case noise profiles have been obtained, using the plural case noise profiles, wherein performing the comparative study comprises identifying at least one location for remedial measures.

3. The method of claim 1, further comprising identifying, with at least one processing unit, a source of noise for the case noise profile, using the plural ease noise profiles.

4. The method of claim 1, wherein the physiological information and the noise information are at least one of obtained or recorded substantially continuously at a common sample rate.

5. The method of claim 1, wherein the noise information is recorded at discrete intervals corresponding to the sample rate of the physiological information, wherein the noise information is recorded based upon at least one of meeting or exceeding a threshold of a noise metric.

6. The method of claim 1, wherein recording the noise information comprises recording noise information on plural noise recording channels.

7. The method of claim 1, wherein recording the noise information comprises recording an aggregate noise signal, wherein the aggregate noise signal is formed from noise information from plural noise acquisition units.

8. The method of claim 1, wherein the noise information includes at least one value of a noise metric, and wherein obtaining the noise information includes determining the at least one value of a noise metric based on data detected by the at least one noise acquisition unit.

9. The method of claim 1, further comprising performing an analysis of the case noise profile using information at least one of contained in or developed from the archive containing the case noise profiles.

10. A method comprising:
obtaining, via at least one physiological sensor, physiological information of a patient, wherein the physiological information is acquired autonomously with the at least one physiological sensor;
acquiring environmental information corresponding to at least one of a time or location at which the physiological information was obtained;
obtaining, via a noise acquisition unit, noise information corresponding to noise occurring during collection of the physiological information, wherein the noise information is acquired autonomously with the noise acquisition unit;
recording the physiological information on at least one physiological recording channel;
recording the noise information on at least one noise recording channel at a sample rate corresponding to a rate used to record the physiological information;
associating, with the at least one processor, the noise information with the environmental information to provide a case noise profile that includes the physiological inthrmation, noise information, and environmental information, wherein the noise information and physiological information are associated without being mixed in the case noise profile; and
performing, with the at least one processor, an analysis of the case noise profile using information at least one of contained in or developed from an archive containing plural case noise profiles, wherein the case noise profile that is analyzed includes both the noise information and the physiological information.

11. The method of claim 10, wherein performing the analysis comprises evaluating if the physiological information is acceptable based on a threshold of a noise metric determined using the plural case noise profiles.

12. The method of claim 10, wherein performing the analysis comprises identifying, with the at least one processing unit, a source of noise for the case noise profile, using the plural case noise profiles.

13. The method of claim 10, wherein the physiological information and the noise information are at least one of obtained or recorded substantially continuously at a common sample rate.

14. The method of claim 10, wherein the noise information is recorded at discrete intervals corresponding to the sample rate of the physiological information, wherein the noise information is recorded based upon at least one of meeting or exceeding a threshold of a noise metric.

15. A system comprising:
an input module configured to:
obtain, autonomously, via at least one physiological sensor, physiological information of a patient;
acquire environmental information corresponding to at least one of a time or location at which the physiological information was obtained;
obtain, autonomously, via a noise acquisition unit, noise information corresponding to noise occurring during collection of the physiological information;
an association module comprising processing circuitry configured to:
record the physiological information on at least one physiological recording channel;
record the noise information on at least one noise recording channel at a sample rate corresponding to a rate used to record the physiological information; and
associate the noise information with the environmental information to provide a case noise profile that includes the physiological information, noise information, and environmental information, wherein the noise information and physiological information are associated without being mixed in the case noise profile; and
an archive module configured to store the case noise profile as part of an archive containing plural case noise profiles, wherein the case noise profile that is stored as part of the archive includes both the noise information and the physiological information.

16. The system of claim 15, wherein the association module is configured to record the physiological information and the noise information substantially continuously at a common sample rate.

17. The system of claim 15, wherein the association module is configured to record the noise information at discrete intervals corresponding to the sample rate of the physiological information, wherein the noise information is recorded based upon at least one of meeting or exceeding a threshold of a noise metric.

18. The system of claim 15, wherein the association module is configured to record an aggregate noise signal, wherein the aggregate noise signal is formed from noise information from plural noise acquisition units.

19. The system of claim 15, wherein the noise information includes at least one value of a noise metric, and wherein at least one of the input module or the association module is configured to determine at least one value of a noise metric based on data detected by the at least one noise acquisition unit.

20. The system of claim 15, further comprising an analysis module comprising processing circuitry configured to perform an analysis of the ease noise profile using information at least one of contained in or developed from an archive containing plural sets of case noise profiles, wherein the analysis includes determining if noise associated with the physiological information satisfies a threshold.

21. The method of claim 1, wherein the noise information is acquired via an antenna.

22. The method of claim 1, wherein the physiological information comprises a first type of physiological signal, and the noise information comprises a second type of physiological signal that is different from the first type of physiological signal.

23. The method of claim 1, wherein each case noise profile is for a corresponding particular patient and procedure, and the archive includes case profiles for different patients.

24. The method of claim 1, further comprising at least one of using the case noise profile to determine a root cause of noise, or comparing a current case noise profile with at least one archived case noise profile.

25. The method of claim 10, wherein each case noise profile is for a corresponding particular patient and procedure, and the archive includes case profiles for different patients.

26. The system of claim 15, wherein each case noise profile is for a corresponding particular patient and procedure, and the archive includes case profiles for different patients.

* * * * *